(12) United States Patent
Wei et al.

(10) Patent No.: US 11,989,518 B2
(45) Date of Patent: May 21, 2024

(54) NORMALIZED PROCESSING METHOD AND APPARATUS OF NAMED ENTITY, AND ELECTRONIC DEVICE

(71) Applicant: BOE TECHNOLOGY GROUP CO., LTD., Beijing (CN)

(72) Inventors: Xiaohong Wei, Beijing (CN); Yongyang Yan, Beijing (CN); Chuan Wang, Beijing (CN); Nan Liu, Beijing (CN); Yiming Lei, Beijing (CN); Hong Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 352 days.

(21) Appl. No.: 17/506,726

(22) Filed: Oct. 21, 2021

(65) Prior Publication Data

US 2022/0129632 A1 Apr. 28, 2022

(30) Foreign Application Priority Data

Oct. 22, 2020 (CN) .......................... 202011138335.1

(51) Int. Cl.
| | |
|---|---|
| *G06F 40/295* | (2020.01) |
| *G06F 16/33* | (2019.01) |
| *G06F 40/247* | (2020.01) |
| *G06N 3/044* | (2023.01) |
| *G16H 70/60* | (2018.01) |

(52) U.S. Cl.
CPC ........ *G06F 40/295* (2020.01); *G06F 16/3344* (2019.01); *G06F 40/247* (2020.01); *G06N 3/044* (2023.01); *G16H 70/60* (2018.01)

(58) Field of Classification Search
CPC .. G06F 40/295; G06F 16/3344; G06F 40/247; G06F 40/279
See application file for complete search history.

(56) References Cited

U.S. PATENT DOCUMENTS

| | | | |
|---|---|---|---|
| 8,533,203 B2* | 9/2013 | Chaudhuri | G06F 40/247 707/728 |
| 9,600,566 B2* | 3/2017 | Ganti | G06F 16/3344 |
| 9,639,518 B1* | 5/2017 | Goodspeed | G06Q 30/0281 |
| 11,163,956 B1* | 11/2021 | De Peuter | G06F 16/3347 |
| 11,604,925 B1* | 3/2023 | Lee | G06N 3/0442 |
| 2013/0346421 A1* | 12/2013 | Wang | G06F 40/295 707/755 |
| 2014/0277921 A1* | 9/2014 | Gujjar | G05B 23/0221 701/32.9 |

(Continued)

*Primary Examiner* — Douglas Godbold
(74) *Attorney, Agent, or Firm* — Dority & Manning, P.A.

(57) ABSTRACT

A normalized processing method of a named entity includes: obtaining first text data; recognizing a named entity from the first text data; determining whether a first standard named entity exists in a standard named entity database according to the named entity; determining the first standard named entity as a normalized representation of the named entity in response to determining that the first standard named entity exists in the standard named entity database; and obtaining a second standard named entity from the standard named entity database and determining an obtained second standard named entity as the normalized representation of the named entity in response to determining that the first standard named entity does not exist in the standard named entity database.

17 Claims, 6 Drawing Sheets

(56) References Cited

U.S. PATENT DOCUMENTS

| 2016/0062983 | A1* | 3/2016 | Jung | G06F 40/295 |
| | | | | 704/9 |
| 2020/0104362 | A1* | 4/2020 | Yang | G06N 5/048 |
| 2023/0205999 | A1* | 6/2023 | Pham | G06N 3/082 |
| | | | | 704/9 |

* cited by examiner

NORMALIZED PROCESSING METHOD AND APPARATUS OF NAMED ENTITY, AND ELECTRONIC DEVICE

CROSS-REFERENCE TO RELATED APPLICATION

This application claims priority to Chinese Patent Application No. 202011138335.1, filed on Oct. 22, 2020, which is incorporated herein by reference in its entirety.

TECHNICAL FIELD

The present disclosure relates to the field of data processing technologies, and in particular, to a normalized processing method and apparatus of a named entity, an electronic device and a storage medium.

BACKGROUND

A named entity refers to as an entity identified by a person's name, an organization name, a location name, and other names. Taking the medical field as an example, a medical named entity refers to various things, phenomena, characteristics, relationships, and processes in the medical field, such as diseases, disease diagnosis, clinical symptoms, examinations, and treatments.

The named entity normalization is a basis of information extraction, and aims to map a natural language description entity in a text to a standard entity name in a standard named entity database in the related field.

SUMMARY

In an aspect, a normalized processing method of a named entity is provided. The normalized processing method of the named entity includes: obtaining first text data; recognizing a named entity from the first text data; determining whether a first standard named entity exists in a standard named entity database according to the named entity; determining the first standard named entity as a normalized representation of the named entity in response to determining that the first standard named entity exists in the standard named entity database; and obtaining a second standard named entity from the standard named entity database and determining an obtained second standard named entity as the normalized representation of the named entity in response to determining that the first standard named entity does not exist in the standard named entity database. The first standard named entity is a standard named entity whose character string matches a character string of the named entity or an extended named entity. The extended named entity is obtained by performing a synonym substitution on at least part of words of the named entity. The second standard named entity is a standard named entity whose word vector similarity to the named entity in the standard named entity database satisfies a preset condition.

In some embodiments, recognizing the named entity from the first text data, includes: deleting a first text in the first text data to obtain second text data, and recognizing the named entity from the second text data. The first text includes at least one stop word and/or at least one designated symbol.

In some embodiments, the second text data is a long text. Recognizing the named entity from the second text data, includes: using a first named entity recognition algorithm to recognize the named entity from the second text data, the first named entity recognition algorithm being a named entity recognition algorithm for the long text.

In some embodiments, before recognizing the named entity from the second text data, recognizing the named entity from the first text data, further includes: determining whether a text length of the second text data is greater than a preset text length threshold; using the second text data as the long text in response to determining that the text length of the second text data is greater than the preset text length threshold.

In some embodiments, the first named entity recognition algorithm includes a named entity recognition algorithm based on a bi-directional long-short term memory network (BiLSTM) and a conditional random field (CRF).

In some embodiments, the second text data is a short text. Recognizing the named entity from the second text data, includes: using a second named entity recognition algorithm to recognize the named entity from the second text data, the second named entity recognition algorithm being a named entity recognition algorithm for the short text.

In some embodiments, before recognizing the named entity from the second text data, recognizing the named entity from the first text data, further includes: determining whether a text length of the second text data is greater than a preset text length threshold; using the second text data as the short text in response to determining that the text length of the second text data is less than or equal to the preset text length threshold.

In some embodiments, the second named entity recognition algorithm includes a named entity recognition algorithm based on a regular expression.

In some embodiments, determining whether the first standard named entity exists in the standard named entity database according to the named entity, includes: searching for the standard named entity whose character string matches the character string of the named entity in the standard named entity database, and searching for the standard named entity whose character string matches the character string of the extended named entity in the standard named entity database in response to determining that the standard named entity whose character string matches the character string of the named entity is not found. The found standard named entity whose character string matches the character string of the named entity or the extended named entity is used as the first standard named entity.

In some embodiments, the extended named entity is obtained by performing a complete synonym substitution on the named entity, and the complete synonym substitution is a synonym substitution on the named entity as a whole.

In some embodiments, the extended named entity is obtained by performing a partial synonym substitution on the named entity, and the partial synonym substitution is a synonym substitution on at least one named entity word segmentation obtained by performing a word segmentation processing on the named entity.

In some embodiments, performing the partial synonym substitution on the named entity, includes: performing the word segmentation processing on the named entity to obtain a plurality of named entity word segmentations; traversing a partial synonym mapping table according to the plurality of named entity word segmentations, and substituting at least one traversed named entity word segmentation for a synonym to obtain the extended named entity.

In some embodiments, obtaining the second standard named entity from the standard named entity database, includes: determining a word vector similarity between each standard named entity in the standard named entity database and the named entity based on a word vector similarity matching algorithm; and determining the standard named entity whose word vector similarity to the named entity in the standard named entity database satisfies the preset condition as the second standard named entity.

In some embodiments, the preset condition is that the word vector similarity between the named entity and the standard named entity reaches a preset similarity threshold, or the preset condition is that the named entity and one standard named entity in the standard named entity database have a highest word vector similarity.

In some embodiments, determining the word vector similarity between each standard named entity in the standard named entity database and the named entity based on the word vector similarity matching algorithm, includes: calculating a length of a longest common subsequence of the named entity and each standard named entity in the standard named entity database; sequencing standard named entities in the standard named entity database to obtain a standard named entity candidate list according to lengths of the longest common subsequences; and sequentially inputting each standard named entity in the standard named entity candidate list and the named entity into a semantic model based on a word vector, so as to obtain the word vector similarity between the named entity and the standard named entity.

In some embodiments, the semantic model based on the word vector includes a bi-directional encoder representation from transformers (BERT) model, and a fully connected layer of the BERT model is implemented by using a softmax classifier or a sigmoid classifier.

In another aspect, a normalized processing apparatus of a named entity is provided. The normalized processing apparatus of the named entity includes: a memory, at least one processor, and computer program instructions stored on the memory and run on the at least one processor. The at least one processor is configured to: obtain first text data, recognize a named entity from the first text data; determine whether a first standard named entity exists in a standard named entity database according to the named entity; determine the first standard named entity as a normalized representation of the named entity in response to determining that the first standard named entity exists in the standard named entity database; and obtain a second standard named entity from the standard named entity database and determine an obtained second standard named entity as the normalized representation of the named entity in response to determining that the first standard named entity does not exist in the standard named entity database. The first standard named entity is a standard named entity whose character string matches a character string of the named entity or an extended named entity. The extended named entity is obtained by performing a synonym substitution on at least part of words of the named entity. The second standard named entity is a standard named entity whose word vector similarity to the named entity in the standard named entity database satisfies a preset condition.

In some embodiments, the at least one processor is further configured to delete a first text in the first text data to obtain second text data, and recognize the named entity from the second text data. The first text includes at least one stop word and/or at least one designated symbol.

In some embodiments, the second text data is a long text. The at least one processor is further configured to use a first named entity recognition algorithm to recognize the named entity from the second text data, the first named entity recognition algorithm is a named entity recognition algorithm for the long text.

In some embodiments, the at least one processor is further configured to determine whether a text length of the second text data is greater than a preset text length threshold before recognizing the named entity from the second text data; and use the second text data as the long text in response to determining that the text length of the second text data is greater than the preset text length threshold.

In some embodiments, the first named entity recognition algorithm includes a named entity recognition algorithm based on a bi-directional long-short term memory network (BiLSTM) and a conditional random field (CRF).

In some embodiments, the second text data is a short text. The at least one processor is further configured to use a second named entity recognition algorithm to recognize the named entity from the second text data, the second named entity recognition algorithm is a named entity recognition algorithm for the short text.

In some embodiments, the at least one processor is further configured to determine whether a text length of the second text data is greater than a preset text length threshold before recognizing the named entity from the second text data; and use the second text data as the short text in response to determining that the text length of the second text data is less than or equal to the preset text length threshold.

In some embodiments, the second named entity recognition algorithm includes a named entity recognition algorithm based on a regular expression.

In some embodiments, the at least one processor is further configured to search for the standard named entity whose character string matches the character string of the named entity in the standard named entity database, and search for the standard named entity whose character string matches the character string of the extended named entity in the standard named entity database in response to determining that the standard named entity whose character string matches the character string of the named entity is not found. The found standard named entity whose character string matches the character string of the named entity or the extended named entity is used as the first standard named entity.

In some embodiments, the extended named entity is obtained by performing a complete synonym substitution on the named entity, and the complete synonym substitution is a synonym substitution on the named entity as a whole.

In some embodiments, the extended named entity is obtained by performing a partial synonym substitution on the named entity, and the partial synonym substitution is a synonym substitution on at least one named entity word segmentation obtained by performing a word segmentation processing on the named entity.

In some embodiments, the at least one processor is further configured to perform the word segmentation processing on the named entity to obtain a plurality of named entity word segmentations; traverse a partial synonym mapping table according to the plurality of named entity word segmentations, and substitute at least one traversed named entity word segmentation for a synonym to obtain the extended named entity.

In some embodiments, the at least one processor is further configured to determine a word vector similarity between each standard named entity in the standard named entity database and the named entity based on a word vector similarity matching algorithm; and determine the standard named entity whose word vector similarity to the named entity in the standard named entity database satisfies the preset condition as the second standard named entity.

In some embodiments, the preset condition is that the word vector similarity between the named entity and the standard named entity reaches a preset similarity threshold, or the preset condition is that the named entity and one standard named entity in the standard named entity database have a highest word vector similarity.

In some embodiments, the at least one processor is further configured to calculate a length of a longest common subsequence of the named entity and each standard named entity in the standard named entity database; sequence standard named entities in the standard named entity database to obtain a standard named entity candidate list according to lengths of the longest common subsequences; and sequentially input each standard named entity in the standard named entity candidate list and the named entity into a semantic model based on a word vector, so as to obtain the word vector similarity between the named entity and the standard named entity.

In some embodiments, the semantic model based on the word vector includes a bi-directional encoder representation from transformers (BERT) model, and a fully connected layer of the BERT model is implemented by using a softmax classifier or a sigmoid classifier.

In yet another aspect, an electronic device is provided. The electronic device includes a memory, a processor, and computer program instructions stored on the memory and run on the processor. When the processor executes the computer program instructions, the electronic device performs one or more steps of the normalized processing method of the named entity as described in any of the above embodiments.

In yet another aspect, a non-transitory computer-readable storage medium is provided. The non-transitory computer-readable storage medium stores computer program instructions that, when executed by a computer (e.g., a normalized processing apparatus of the named entity), cause the computer to perform one or more steps of the normalized processing method of the named entity as described in any one of the above embodiments.

In yet another aspect, a computer program product is provided. The computer program product includes computer program instructions that are stored in a non-transitory computer-readable storage medium. When executed by a computer (e.g., a normalized processing apparatus of the named entity), the computer program instructions cause the computer to perform one or more steps of the normalized processing method of the named entity as described in any one of the above embodiments.

BRIEF DESCRIPTION OF THE DRAWINGS

In order to describe technical solutions in the present disclosure more clearly, the accompanying drawings to be used in some embodiments of the present disclosure will be introduced briefly below. However, the accompanying drawings to be described below are merely accompanying drawings of some embodiments of the present disclosure, and a person of ordinary skill in the art may obtain other drawings according to these drawings. In addition, the accompanying drawings in the following description may be regarded as schematic diagrams, and are not limitations on actual sizes of products, actual processes of methods and actual timings of signals to which the embodiments of the present disclosure relate.

DETAILED DESCRIPTION

Figure 1:
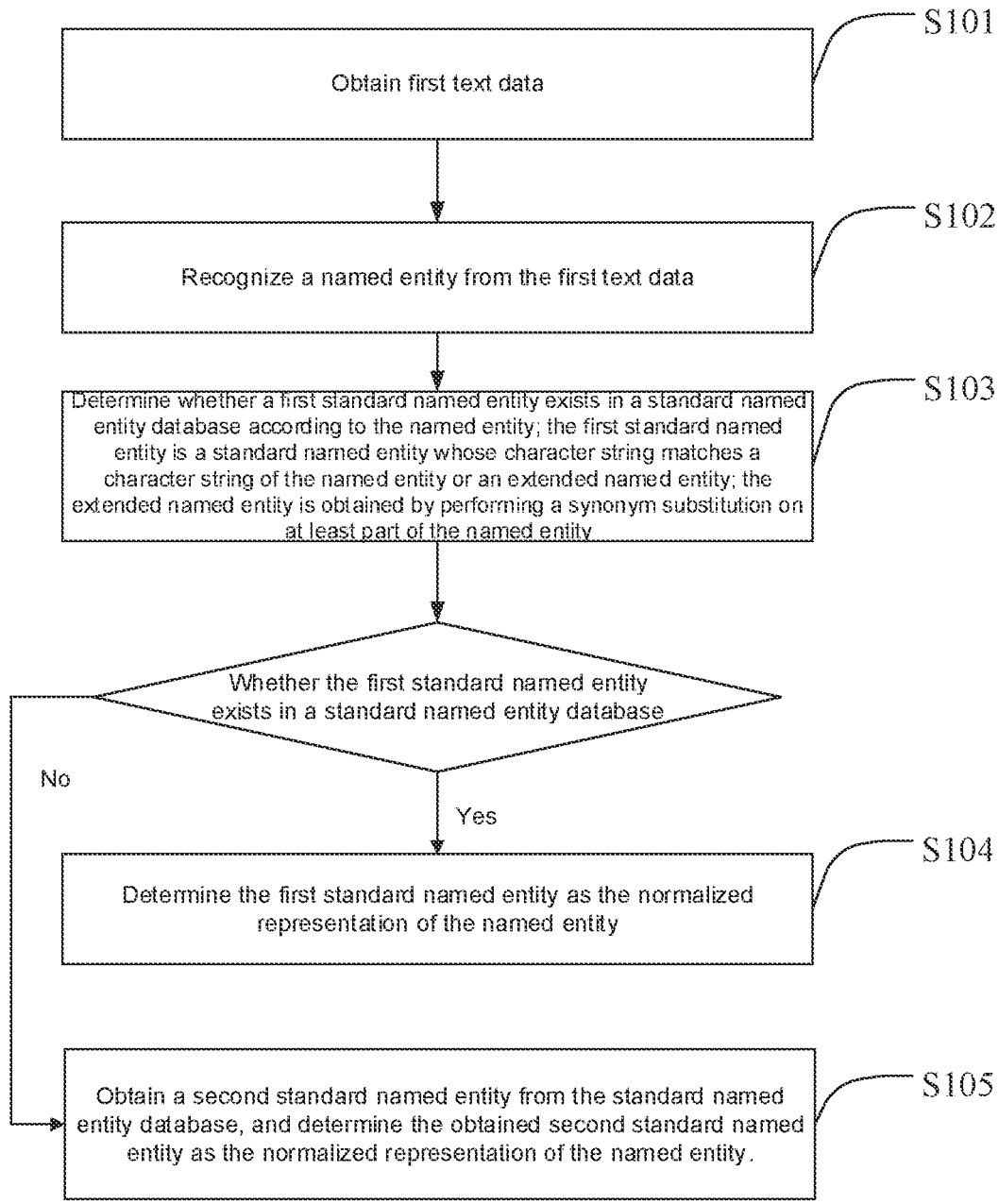
FIG. 1 is a flow diagram of a normalized processing method of a named entity, in accordance with some embodiments.

Technical solutions in some embodiments of the present disclosure will be described clearly and completely below with reference to the accompanying drawings. However, the described embodiments are merely some but not all embodiments of the present disclosure. All other embodiments obtained by a person of ordinary skill in the art on a basis of the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to." In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics may be included in any one or more embodiments or examples in any suitable manner.

Hereafter, the terms "first" and "second" are used for descriptive purposes only, and are not to be construed as indicating or implying the relative importance or implicitly indicating the number of indicated technical features. Thus, a feature defined with "first" or "second" may explicitly or implicitly include one or more of the features. In the description of the embodiments of the present disclosure, the term "a plurality of" or "the plurality of" means two or more unless otherwise specified.

The phrase "at least one of A, B and C" has the same meaning as the phrase "at least one of A, B or C", and they both include the following combinations of A, B and C: only A, only B, only C, a combination of A and B, a combination of A and C, a combination of B and C, and a combination of A, B and C.

The phrase "A and/or B" includes the following three combinations: only A, only B, and a combination of A and B.

As used herein, the term "if" is optionally construed as "when" or "in a case where" or "in response to determining that" or "in response to detecting", depending on the context. Similarly, the phrase "if it is determined that" or "if [a stated condition or event] is detected" is optionally construed as "in a case where it is determined that" or "in response to determining that" or "in a case where [the stated condition or event] is detected" or "in response to detecting [the stated condition or event]", depending on the context.

The use of the phrase "applicable to" or "configured to" herein means an open and inclusive language, which does not exclude devices that are applicable to or configured to perform additional tasks or steps.

In addition, the use of the phrase "based on" is meant to be open and inclusive, since a process, step, calculation or other action that is "based on" one or more of the stated conditions or values may, in practice, be based on additional conditions or values exceeding those stated.

Embodiments of the present disclosure provide a normalized processing method and apparatus of a named entity, an electronic device, and a storage medium, which will be illustrated below with reference to the accompanying drawings.

FIG. 1 is a flow diagram of a normalized processing method of a named entity in accordance with some embodiments. As shown in FIG. 1, the normalized processing method of the named entity may include the following steps.

In S101, first text data is obtained.

The first text data may refer to various text data input by a user to an electronic device. The first text data may be medical text data, or text data in other fields or industries, for example, text data in fields of smart customer service or e-commerce.

In the following description of the embodiments of the present disclosure, an example in which the first text data is the medical text data and a normalized processing of the medical named entity is performed is mainly taken for illustration, but the present disclosure is not limited to the normalized processing of the medical named entity, and the method may also be used for a normalized processing of a named entity in any other field or industry.

In S102, a named entity is recognized from the first text data.

The named entity can include one word (group) or a plurality of word segmentations (i.e., named entity word segmentations). For example, the named entity may be represented in a form of a character string. In the case where the named entity includes the word (group), the character string used for representing the named entity may be a character string with independent meaning; and in the case where the named entity includes the plurality of named entity word segmentations, the character string used for representing the named entity may include a plurality of character sub-strings, and each named entity word segmentation corresponds to one character sub-string, that is, each named entity word segmentation is represented by a corresponding character sub-string.

Figure 2:
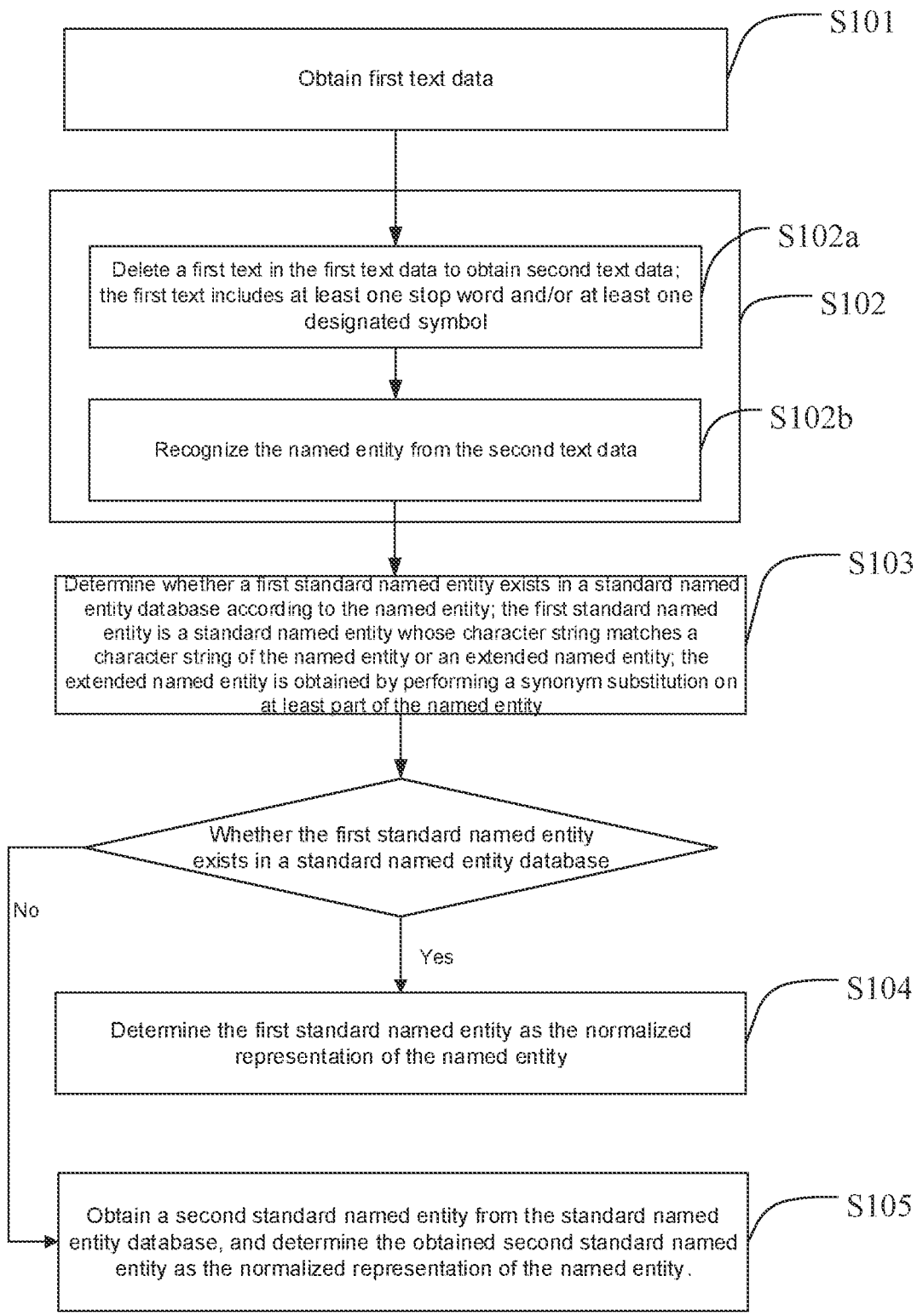
FIG. 2 is a flow diagram of another normalized processing method of a named entity, in accordance with some embodiments.

Generally, the first text data contains some words or symbols that are meaningless for a named entity recognition, or words or symbols that affect the named entity recognition. Based on this, in some embodiments, as shown in FIG. 2, S102 may include S102a and S102b.

In S102a, a first text in the first text data is deleted to obtain second text data. The first text includes at least one stop word and/or at least one designated symbol.

The second text data is text data obtained by deleting some or all stop words and/or designated symbols from the first text data.

For the stop word, those skilled in the art may discover a difference between a standard named entity and a common text description through observation, analysis and comparison in advance. The stop word may be determined according to the difference between the standard named entity and the common text description, so as to construct a stop word table.

Here, the first text data being the medical text data is taken for description. For example, a common text description corresponding to a standard named entity "pelvic fracture" is "multiple pelvic fractures". Through comparison, there is a word "multiple" in the common text description as compared to the standard named entity, and thus the word "multiple" may be determined as the stop word. For another example, common text descriptions corresponding to a standard named entity "pleural effusion" may include "large pleural effusion", "small pleural effusion" and "moderate pleural effusion". Through comparison, there are words such as "large", "small" and "moderate" in the common text description as compared to the standard named entity, and thus the words "large", "small" and "moderate" each may be determined as the stop word.

Through continuous accumulation for a long time, the stop word table in the related field (e.g., the medical field) may be formed, as shown in Table 1 below.

TABLE 1

| Standard named entity | Common text description | Stop word |
|---|---|---|
| Pelvic fracture | Multiple pelvic fractures | Multiple |
| Pleural effusion | Large pleural effusion, small pleural effusion, moderate pleural effusion | Large, small, moderate |
| . . . | . . . | . . . |

After the first text data has been obtained, the stop word in the first text data corresponding to the common text description may be deleted according to a correspondence relationship among the standard named entity, the common text description, and the stop word in the stop word table, so as to avoid the stop word in the first text data affecting the accuracy of the named entity recognition and subsequent normalized processing.

In addition, some meaningless designated symbols in the first text data, such as the punctuation mark "," or the special symbol "*", may also be deleted. The designated symbol may be flexibly set according to actual applications, which is not limited in the embodiments of the present disclosure. The at least one designated symbol in the first text data is deleted, so that the accuracy of the named entity recognition and the subsequent normalized processing may also be improved to a certain extent.

In S102b, the named entity is recognized from the second text data.

Since the first text data is the text data input by the user to the electronic device, the first text data may be classified as a long text and a short text according to the text length of the first text data. It will be understood that, the second text data obtained by deleting the at least one stop word and/or the at least one designated symbol in the S102a may also be classified as the long text and the short text.

Generally, whether the second text data is the long text or the short text may be determined according to a preset text length threshold. In addition, the text length of the second text data may refer to the number of words included in the second text data, or refer to the number of characters included in the second text data, which may be set according to actual needs. For example, before recognizing the named entity from the second text data, it is determined whether a text length of the second text data is greater than the preset text length threshold; the second text data is used as the long text in response to determining that the text length of the second text data is greater than the preset text length threshold; and the second text data is used as the short text in response to determining that the text length of the second text data is less than or equal to the preset text length threshold.

For example, assuming that the preset text length threshold is 10, for medical text data A that "(1 dental calculus I° is formed by plaque and tartar that are deposited on a tooth surface by mineral salts in saliva, and the dental calculus is generally not easy to remove", it is obvious that the text length of the medical text data A is greater than the preset text length threshold, and thus it may be determined that the medical text data A is the long text.

For another example, assuming that the preset text length threshold is 10, for medical text data B that "【4】hyperplasia of bilateral mammary glands:", it is obvious that the text length of the medical text data B is less than the preset text length threshold, and thus it may be determined that the medical text data B is the short text.

When the named entity is recognized from the second text data, for the long text and the short text, different methods may be used to recognize the named entity, so as to improve the recognition efficiency.

In some examples, if the second text data is the long text, a first named entity recognition algorithm is used to recognize the named entity from the second text data.

The first named entity recognition algorithm may be any named entity recognition algorithm for the long text provided in the related art. For example, the first named entity recognition algorithm may be a named entity recognition algorithm based on a conditional random field (CRF), or may be a named entity recognition algorithm based on a bi-directional long-short term memory network (BiLSTM) and the CRF (i.e., BiLSTM+CRF). The CRF is a common sequence labeling algorithm that may be used for tasks such as part-of-speech tagging, word segmentation, and named entity recognition. (BiLSTM+CRF) is a popular sequence labeling algorithm at present, which combines the BiLSTM and the CRF together, so that a model may not only consider relevance between adjacent sequences like the CRF, but also have feature extraction and fitting capabilities of the long-short term memory (LSTM). In the embodiment of the present disclosure, the first named entity recognition algorithm may be implemented with reference to any CRF algorithm or (BiLSTM+CRF) algorithm provided in the related art.

For example, for the medical text data A that "(1 dental calculus I° is formed by plaque and tartar that are deposited on the tooth surface by mineral salts in saliva, and the dental calculus is generally not easy to remove", the medical text data A may be input into a first named entity recognition algorithm model for recognition. The medical named entity "dental calculus" may be obtained after recognition in the first named entity recognition algorithm model.

For another example, for the medical text data C that "ametropia of both eyes (corrected vision of the right eye is lower than a normal standard 5.0/1.0), please pay attention to eye hygiene and do eye exercises frequently", the medical text data C may be input into the first named entity recognition algorithm model for recognition. The medical named entity "ametropia" may be obtained after the recognition in the first named entity recognition algorithm model.

In some other examples, if the second text data is the short text, a second named entity recognition algorithm is used to recognize the named entity from the second text data.

The second named entity recognition algorithm may be any named entity recognition algorithm for the short text provided in the related art.

In practical applications, the short text usually has some characteristic characters. For example, in short texts such as "【4】hyperplasia of bilateral mammary glands:", "【12】ametropia", "1, [low diastolic pressure]", and "1, [obesity]", there are characteristic characters "【", "】", ",", ":", "[", "]", etc.

In this case, the second named entity recognition algorithm may include a named entity recognition algorithm based on a regular expression. The named entity recognition algorithm based on the regular expression refers to an algorithm that uses the regular expression to recognize the named entity. For different text features, a corresponding regular expression may be used to recognize the named entity contained therein.

For example, for the text data "【4】hyperplasia of bilateral mammary glands:", "【12】ametropia:", the named entities "hyperplasia of bilateral mammary" and "ametropia" may be obtained through processing of a regular expression r'【\d{1,2}】(*):'.

For another example, for the text data "1, [low diastolic pressure]" and "1, [obesity]", the named entities "low diastolic pressure" and "obesity" may be obtained through processing of a regular expression r'^\d{1,2},\[\(*)\]'.

The above are exemplary descriptions. In specific applications, those skilled in the art may set or select an appropriate regular expression according to specific text feature of the short text to recognize and obtain the named entity.

Through the above implementation manners, the named entity recognition may be performed in a differential and targeted manner for the long text and the short text, so as to improve the accuracy and the efficiency of the named entity recognition.

Of course, in some embodiments, the named entity being recognized from the first text data in S102 may be implemented by directly recognizing the named entity from the first text data, without deleting the at least one stop word and/or the at least one designated symbol in S102a, and the recognition method may still adopt the first named entity recognition algorithm or the second named entity recognition algorithm, which will not be repeated here.

In S103, it is determined whether a first standard named entity exists in a standard named entity database according to the named entity. The first standard named entity is a standard named entity whose character string matches a character string of the named entity or an extended named entity. The extended named entity is obtained by performing a synonym substitution on at least part of words of the named entity.

That is, the first standard named entity is the standard named entity whose character string matches the character string of the named entity, or, the first standard named entity is the standard named entity whose character string matches the character string composed of all character sub-strings of the extended named entity. The character string of the extended named entity may be obtained by substituting at least part of all the character sub-strings of the named entity. In other words, at least part of the character sub-strings of the extended named entity is obtained by substituting at least part of the character sub-strings of the named entity.

Since a text matching has characteristics of simplicity and high efficiency, in the embodiments of the present disclosure, a text matching (i.e., a character string matching) is performed on the named entity recognized in S102 using a text matching rule method.

Figure 3:
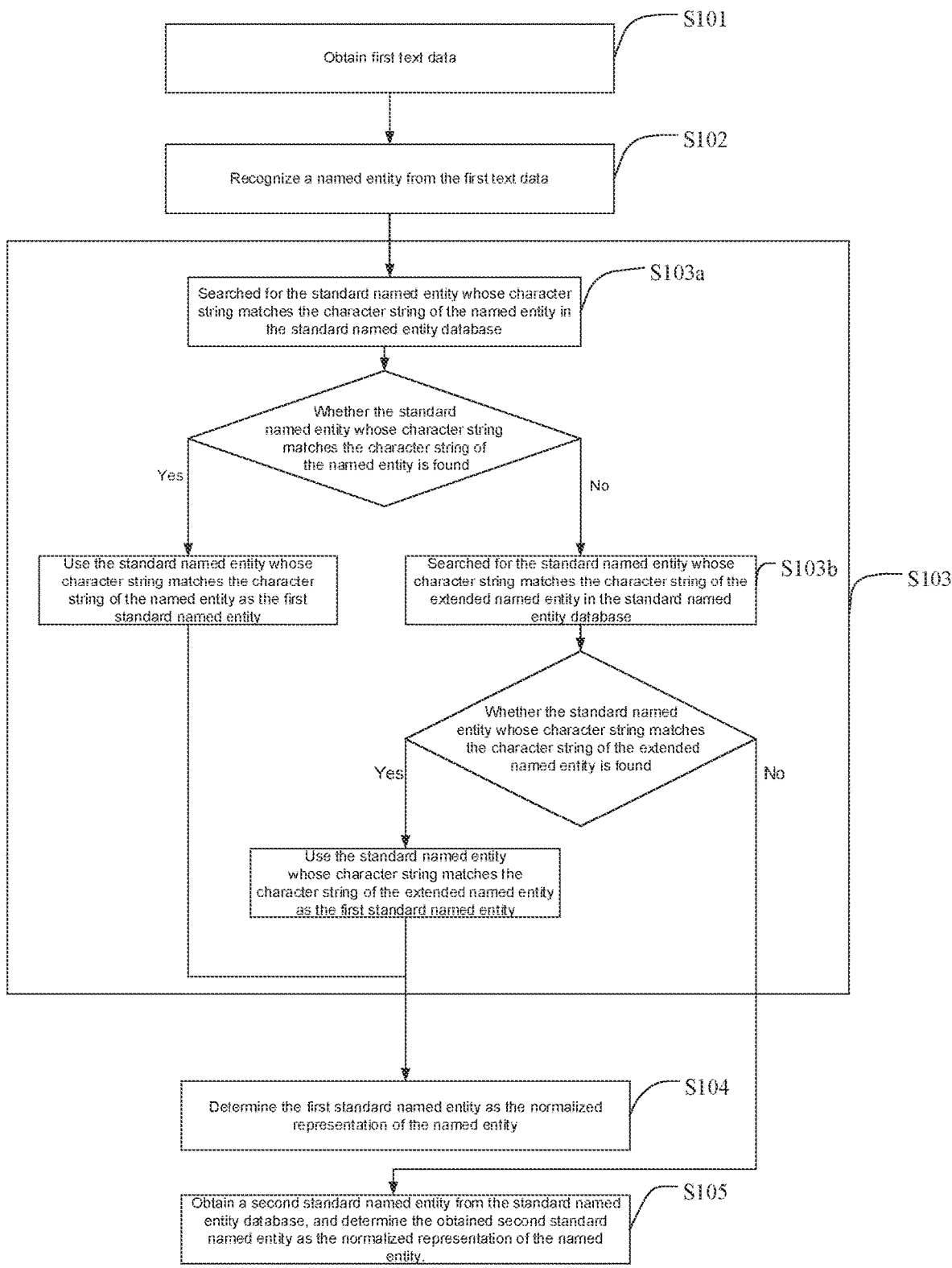
FIG. 3 is a flow diagram of yet another normalized processing method of a named entity, in accordance with some embodiments.

In some embodiments, as shown in FIG. 3, S103 may include S103a and S103b.

In S103a, the standard named entity whose character string matches the character string of the named entity is searched for in the standard named entity database.

The character string of the named entity matches the character string of the standard named entity, which means that a text description of the named entity is identical to a text description of the standard named entity, or a matching degree between the text description of the named entity and the text description of the standard named entity reaches a preset threshold to make them sufficiently similar.

If the standard named entity whose character string matches the character string of the named entity is found, the standard named entity whose character string matches the character string of the named entity is used as the first standard named entity.

In other words, if the standard named entity whose character string matches the character string of the named entity is found in the standard named entity database, it means that the named entity recognized in S102 is the standard named entity, which may be used as a normalized representation of the named entity without performing the subsequent operation S103b.

In S103b, the standard named entity whose character string matches the character string of the extended named entity is searched for in the standard named entity database in response to determining that the standard named entity whose character string matches the character string of the named entity is not found.

It is easy to understand that in actual natural language expressions, the expression of the named entity is not unique, and there are many synonymous expressions. Therefore, an expression that matches the character string of the named entity may not exist in the standard named entity database, so that the standard named entity may not be obtained only based on character string the named entity.

On this basis, the named entity may be further extended to obtain the extended named entity, and then the character string matching is performed between the standard named entity in the standard named entity database and the extended named entity to obtain the standard named entity whose character string matches the character string of the extended named entity.

For example, the embodiments of the present disclosure provide two extension methods of the named entity. One is a complete synonym substitution, that is, substituting the named entity as a whole with synonyms, and the other is a partial synonym substitution, that is, substituting at least part of the named entity word segmentation (i.e., at least one named entity word segmentation) of the named entity.

For the complete synonym substitution, those skilled in the art may construct a complete synonym mapping table in advance according to actual needs, and the complete synonym mapping table is shown in Table 2 below.

TABLE 2

| Standard named entity | Synonym 1 | Synonym 2 |
|---|---|---|
| Overweight | Body Mass index (BMI) ≥ 24 | Increased body mass index |
| $C^{14}$ urea breath test positive | Helicobacter pylori test (breath test) positive | Helicobacter pylori antibody test positive |
| Low vision | Poor vision | Binocular vision is lower than normal standard |

Generally, the semantics of a word and the semantics of a sentence are abstractions on the texts. A computer needs to be supported by continuously acquired knowledge, so as to infer information of the synonym from a small amount of words. Therefore, the complete synonym mapping table will be collected manually by business personnel to ensure a high accuracy rate.

However, due to a flexibility of natural language, for some long-tailed data (e.g., some categories in a data set occupy most data, and remaining categories each occupies little data, so that the data of the categories with little data is called the long-tailed data), it has low probability of appearance, which is difficult to guarantee a recall rate (the recall rate refers to a ratio of samples that are predicted as positive to total positive samples). In this regard, for each specific case, a word may be added to the complete synonym mapping table manually to perfect the complete synonym mapping table shown in the Table 2.

As shown in Table 2, for example, a standard named entity corresponding to a named entity such as "BMI 24" or "increased body mass index" may be "overweight"; and a standard named entity corresponding to a named entity such as "*Helicobacter pylori* test (breath test) positive" or "*Helicobacter pylori* antibody test positive" may be "$C^{14}$ urea breath test positive".

According to the complete synonym mapping table shown in Table 2, it is possible to perform the complete synonym substitution on the named entity to obtain a completely substituted extended named entity. For example, the completely substituted extended named entity "overweight" is obtained after performing the complete synonym substitution on the named entity "BMI≥24". For another example, the completely substituted extended named entity "$C^{14}$ urea breath test positive" is obtained after performing the complete synonym substitution on the named entity "*Helicobacter pylori* antibody test positive".

After the completely substituted extended named entity is obtained through the complete synonym substitution, if the standard named entity whose character string matches the character string of the completely substituted extended named entity is found in the standard named entity database, the standard named entity whose character string matches the character string of the completely substituted extended named entity may be used as the first standard named entity corresponding to the named entity recognized in S102.

It is easy to understand that if the character string of the completely substituted extended named entity can match a character string of a standard named entity in the standard named entity database, it is not necessary to perform the partial synonym substitution on the named entity to obtain a partially substituted extended named entity, and to perform the character string matching between the partially substituted extended named entity and the standard named entity in the standard named entity database. In this way, the efficiency of the character string matching between the extended named entity and the standard named entity may be improved.

Of course, if the standard named entity whose character string matches the character string of the completely substituted extended named entity is not found in the standard named entity database, or there is no complete synonym of the named entity in the complete synonym mapping table, the partial synonym substitution may be performed on the named entity to obtain the partially substituted extended named entity, and the standard named entity whose character string matches the character string of the partially substituted extended named entity is obtained from the standard named entity database.

Compared with the complete synonym substitution, the partial synonym substitution will be implemented through a word segmentation processing on the named entity first, and then substituting word segmentations separately. Therefore, the partial synonym substitution for the named entity may include step 1 and step 2.

In step 1, the word segmentation processing is performed on the named entity to obtain a plurality of named entity word segmentations.

For example, it is assumed that the named entity recognized in S102 is "high-density lipoprotein cholesterol elevated", and four named entity segmentation words [high density, lipoprotein, cholesterol, elevated] may be obtained by performing the word segmentation processing on the named entity.

In step 2, a partial synonym mapping table is traversed according to the plurality of named entity word segmentations, and at least one traversed named entity word segmentation is substituted for a synonym to obtain the partially substituted extended named entity.

For the partial synonym substitution, similar to the complete synonym substitution, those skilled in the art may also construct a partial synonym mapping table in advance according to actual needs, which is shown in Table 3 below.

TABLE 3

| Word segmentation | Synonym 1 | Synonym 2 | Synonym 3 |
| --- | --- | --- | --- |
| Elevate | Raise | Increase | High |
| Reduce | Decrease | Decline | Low |
| Unclear boundary | Blurred margin | \ | \ |
| Calcification focus | Calcification | Scleroma calcification | \ |

After the plurality of named entity word segmentations are obtained according to step 1, it may be possible to search for whether there is a synonym corresponding to each named entity word segmentation in the partial synonym mapping table (referring to the Table 3) for each named entity word segmentation obtained in step 1. If there is the synonym corresponding to the named entity word segmentation in the partial synonym mapping table, the named entity word segmentation is substituted for the corresponding synonym.

For example, for the named entity word segmentation "elevated" in the four named entity word segmentations of [high density, lipoprotein, cholesterol, elevated], there is the synonym 1 "raised" in the partial synonym mapping table. After the named entity word segmentation "elevated" is substituted, the named entity word segmentations are updated to obtain [high density, lipoprotein, cholesterol, raised], and thus a partially substituted extended named entity "high density lipoprotein cholesterol raised" is obtained by combining the updated named entity word segmentations.

In this case, the standard named entity whose character string matches the character string of the partially substituted extended named entity "high density lipoprotein cholesterol raised" may be searched for in the standard named entity database. If it can be found, the standard named entity whose character string matches the character string of the partially substituted extended named entity "high density lipoprotein cholesterol raised" is used as the first standard named entity, and the traversal operation of step 2 is ended.

If it cannot be found, step 2 is repeatedly performed and the partial synonym substitution is continued until the standard named entity whose character string matches the character string of the partially substituted extended named entity is found, or the traversal is finished.

For example, the named entity word segmentation "elevated" in the four named entity word segmentations of [high density, lipoprotein, cholesterol, elevated] also has the synonym 2 "increased" in the partial synonym mapping table. After the named entity word segmentation "elevated" is substituted, the named entity word segmentations are updated to obtain [high density, lipoprotein, cholesterol, increased], and thus a partially substituted extended named entity "high density lipoprotein cholesterol increased" is obtained by combining the updated named entity word segmentations. In this case, the standard named entity whose character string matches the character string of the partially substituted extended named entity "high density lipoprotein cholesterol increased" may be found in the standard named entity database. Subsequent steps will not be repeated here.

Through the implementation manners, the first standard named entity may be matched through the complete synonym substitution or the partial synonym substitution, which may improve a success rate of the text matching. If the text has been matched successfully, there is no need to perform the subsequent steps, thereby improving the efficiency and success rate of the named entity normalization.

Through the complete synonym substitution, the obtained extended named entity is similar to an original meaning of the named entity, and the first standard named entity obtained based on the complete substituted extended named entity has a high accuracy. In a case where the first standard named entity cannot be matched based on the complete synonym substitution, the partial synonym substitution may be used to determine the extended named entity, and there is a high probability to match and obtain the first standard named entity based on the partial substituted extended named entity, which may improve the matching success rate.

In S104, in response to determining that the first standard named entity exists in the standard named entity database, the first standard named entity is determined as the normalized representation of the named entity.

In S105, in response to determining that the first standard named entity does not exist in the standard named entity database, a second standard named entity is obtained from the standard named entity database, and the obtained second standard named entity is determined as the normalized representation of the named entity. The second named entity is a standard named entity whose word vector similarity to the named entity satisfies a preset condition in the standard named entity database.

Figure 4:
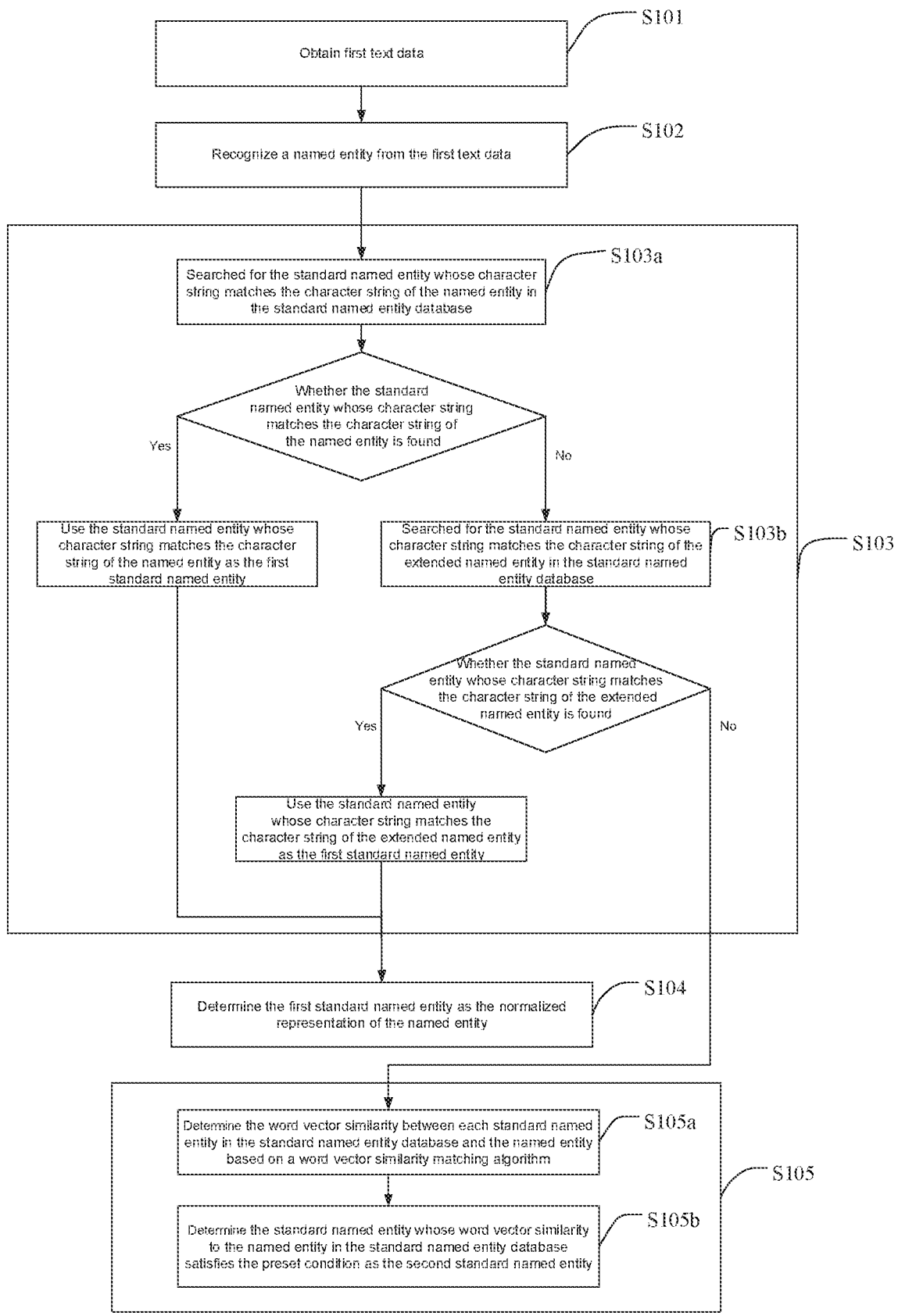
FIG. 4 is a flow diagram of yet another normalized processing method of a named entity, in accordance with some embodiments.

In some embodiments, as shown in FIG. 4, obtaining the second standard named entity from the standard named entity database may include S105a and S105b.

In S105a, the word vector similarity between each standard named entity in the standard named entity database and the named entity is determined based on a word vector similarity matching algorithm.

In step (1), a length of the longest common subsequence (LOS) of the named entity and each standard named entity in the standard named entity database is calculated.

For example, a LOS algorithm may be used to obtain the LOS of the named entity and each standard named entity in the standard named entity database according to the named entity recognized in S102.

For example, the LOS of the named entity "cystic fibrosis" and the standard named entity "cystic fibrosis with lung manifestations" is "cystic fibrosis", and a length of the LOS is 15.

In step (2), standard named entities in the standard named entity database are sequenced according to the length of the LOS between the named entity and each standard named entity in the standard named entity database to obtain a standard named entity candidate list.

According to step (1), the length of the LOS of the named entity and each standard named entity in the standard named entity database may be calculated. The longest common subsequences of the named entity and standard named entities do not necessarily have the same length. According to the length of the LOS, standard named entities in the standard named entity database are sequenced (e.g., in a descending order of length), and the standard named entity candidate list may be obtained.

It is easy to understand that the length of the LOS is long, and the similarity between the named entity and the standard named entity is not necessarily high, but a probability of high similarity is high. Based on this, the longer the length of the LOS is, the higher the probability of successful matching between the named entity and the standard named entity is. Therefore, the standard named entities in the standard named entity database according to the lengths of the longest common subsequences are sequenced, so that a similarity between a standard named entity with a long length of LOS and the named entity may be determined first, and thus the second standard named entity may be matched and obtained fast, thereby improving the success rate and efficiency of the named entity normalization.

In step (3), each standard named entity in the standard named entity candidate list and the named entity are sequentially input into a semantic model based on a word vector to obtain the word vector similarity between the named entity and each standard named entity.

The semantic model based on the word vector may be any semantic model based on a word vector technology provided in the related art. The word vector technology converts a word in natural language into a dense vector, and words with similar semantics will be represented by similar vectors. For example, the semantic model based on the word vector may include a model based on statistics, such as a co-occurrence matrix model and a singular value decomposition (SVD) model. The semantic model based on the word vector may further include a language model based on the neural network, such as word2vec, glove, embeddings from language models (ELMo), and bi-directional encoder representation from transformers (BERT).

The BERT model is a bi-directional encoder representation model with Transformers as a main architecture. The BERT model has a high accuracy and a simple interface for downstream tasks, which solves a problem that a traditional word vector technology has high acquisition cost and is difficult to learn complex context representation.

Therefore, in some embodiments of the present disclosure, the semantic model based on the word vector may be the BERT model.

When the BERT model is used to determine the word vector similarity between the named entity and each standard named entity, a pre-trained BERT model may be obtained first, and then fine-tuning may be performed on the BERT model before applying the BERT model. The fine-tuning may include rewriting read data class according to a data format or using existing data read functions to modify the data format, so as to meet requirements for semantic analysis of the named entity and the standard named entity in some embodiments of the present disclosure. In other words, the fine-tuning may refer to replacing an input layer of the network (that is, input data, including the named entity and the standard named entity), and using new input data for model training.

Of course, the fine-tuning may be performed on all layers or some layers. Generally, general features of the text are extracted by the front layers, and features related to a specific category are extracted by the back layers. Therefore, it is needed to fine-tune the back layers only during the fine-tuning, which has an advantage of being able to train a model quickly. That is, a relatively small amount of data may be used to achieve a good training effect.

After the fine-tuning, each standard named entity in the standard named entity candidate list and the named entity may be input into the BERT model in pairs, so that the standard named entity and the named entity input into the model may be converted into a word vector sequence through the BERT model, which facilitates a subsequent analysis, based on the word vector sequence, of the semantic similarity between a word vector sequence of the named entity and a word vector sequence of the standard named entity.

In some embodiments, a fully connected layer of the BERT model may be implemented by using a softmax classifier or a sigmoid classifier.

The sigmoid classifier may map a real value to an interval of (0, 1) (of course, it may also be an interval of (−1, 1)), which may be used for a binary classification. The softmax classifier may map a k-dimensional real value vector (a1, a2, a3, a4 . . . ) to a constant set (b1 b2, b3, b4 . . . ), wherein bi (i is an integer greater than 0) is a constant within a range of 0 to 1, and then multi-classification tasks may be performed according to a magnitude of bi, such as taking one dimension with the largest weight.

In this way, through the softmax classifier or the sigmoid classifier, the model training may be performed on the word vector sequence of the named entity and the word vector sequence of the standard named entity, and the semantic similarity (the word vector similarity) between the word vector sequence of the named entity and the word vector sequence of the standard named entity may be determined.

In S105b, the standard named entity whose word vector similarity to the named entity in the standard named entity database satisfies the preset condition is determined as the second standard named entity.

The second standard named entity is determined as the normalized representation of the named entity.

The preset condition may be that the word vector similarity between the named entity and the standard named entity reaches a preset similarity threshold, or the preset condition may be that the named entity and one standard named entity have the highest word vector similarity, which may both make the purpose of the embodiments of the present disclosure achieved and be flexibly set by those skilled in the art according to actual needs.

For example, the preset condition may be set to be that the named entity and one standard named entity have the highest word vector similarity. That is, in some embodiments of the present disclosure, the standard named entity whose word vector similarity to the named entity is the highest in the standard named entity database may be determined as the second standard named entity.

Through the above implementation manners, the semantic analysis for the word vector may be performed on the named entity and each standard named entity in the standard named entity database based on the word vector similarity matching algorithm (e.g., the BERT model), so as to obtain the second standard named entity, thereby improving the accuracy of the named entity normalization.

In summary, the normalized processing method of the named entity provided by some embodiments of the present disclosure is not limited to a single processing method (e.g., the text matching rule or the word vector similarity matching algorithm), but combines the text matching rule method and the word vector similarity matching algorithm. Firstly, the text matching rule that is relatively simple (e.g., the character string matching) is used for preliminary matching; if the matching fails by using the text matching rule, the word vector similarity matching algorithm is used for matching. As a result, an amount of data preparation for the text matching rule method may be reduced effectively, and the implementation cost may also be reduced.

In addition, since the text matching rule may quickly normalize some named entities, it may also improve an overall implementation efficiency. For the named entities that fail to match by the text matching rule, the word vector similarity matching algorithm is used to match to ensure the accuracy. Therefore, requirements of accuracy, efficiency and cost can be all taken into consideration. That is, it may be possible to ensure the accuracy, the high implementation efficiency and the low implementation cost.

The normalized processing method of the named entity may be applied to a normalization of the medical named entity. The text matching rule and the word vector similarity matching algorithm are combined, so that once a medical named entity is given, a corresponding standard named entity in a medical standard named entity database may be obtained. The normalized processing method of the named entity may accurately map the natural language description in the text data to the standard named entity in the given medical standard named entity database, which provides a basic implementation manner for application fields such as medical knowledge mining, medical intelligent robots, and medical clinical decision support systems.

In some embodiments of the present disclosure, a normalized processing apparatus of a named entity is also provided. The normalized processing apparatus of the named entity provided in the embodiments of the present disclosure may implement the normalized processing method of the named entity, and the normalized processing apparatus may be implemented by software, hardware, or a combination of software and hardware. For example, the normalized processing apparatus may include integrated or separate function modules or units to execute corresponding steps in the above method.

Figure 5:
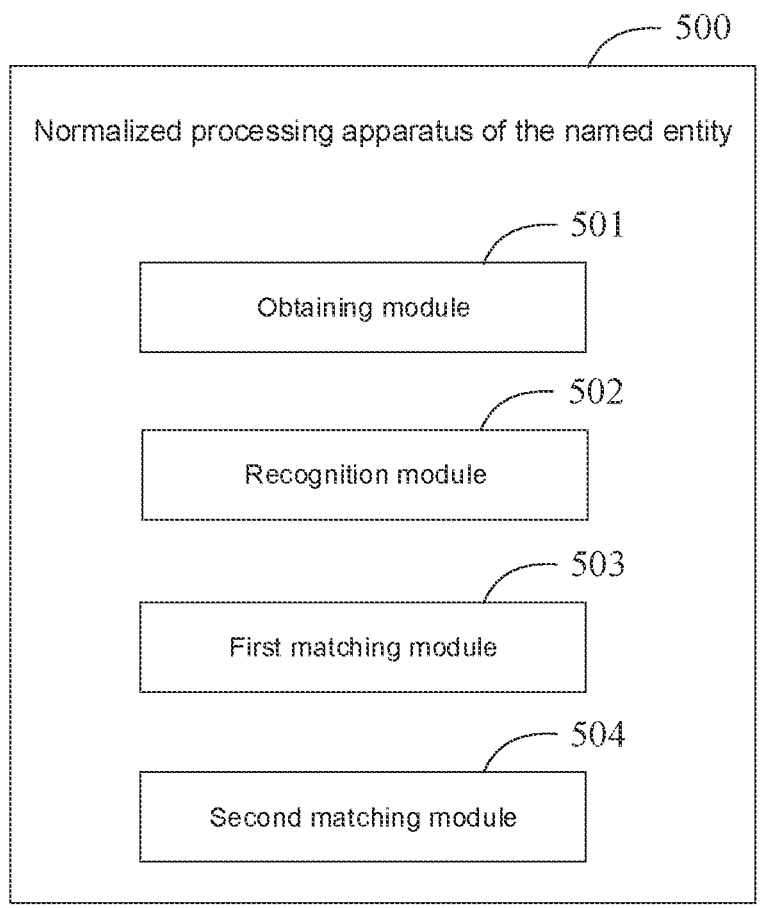
FIG. 5 is a schematic diagram of a normalized processing apparatus of a named entity, in accordance with some embodiments.

For example, FIG. 5 is a schematic diagram of the normalized processing apparatus of the named entity provided by some embodiments of the present disclosure. Since the normalized processing apparatus is used to implement the normalized processing method, it is described in a relatively simple manner, and for related contents, reference may be made to the corresponding description of the method embodiments. The apparatus embodiments described below are merely illustrative.

As shown in FIG. 5, the normalized processing apparatus 500 of the named entity provided by some embodiments of the present disclosure may include an obtaining module 501, a recognition module 502, a first matching module 503 and a second matching module 504.

The obtaining module 501 is configured to obtain the first text data.

The recognition module 502 is configured to recognize the named entity from the first text data.

The first matching module 503 is configured to determine whether the first standard named entity exists in the standard named entity database according to the named entity, and determine the first standard named entity as the normalized representation of the named entity in response to determining that the first standard named entity exists in the standard named entity database. The first standard named entity is a standard named entity whose character string matches the character string of the named entity or the extended named entity. The extended named entity is obtained by performing the synonym substitution on at least part of words of the named entity.

The second matching module 504 is configured to obtain the second standard named entity from the standard named entity database, and determine the second standard named entity as the normalized representation of the named entity in response to determining that the first standard named entity does not exist in the standard named entity database. The second standard named entity is a standard named entity whose word vector similarity to the named entity satisfies the preset condition in the standard named entity database.

In some embodiments, the recognition module 502 is further configured to delete a first text in the first text data to obtain second text data, and recognize the named entity from the second text data. The first text includes at least one stop word and/or at least one designated symbol.

In some embodiments, the recognition module 502 is further configured to determine whether the text length of the second text data is greater than the preset text length threshold, use the second text data as the long text in response to determining that the text length of the second text data is greater than the preset text length threshold, and use the second text data as the short text in response to determining that the text length of the second text data is less than or equal to the preset text length threshold.

The recognition module 502 is further configured to recognize the named entity from the second text data by using the first named entity recognition algorithm in a case where the second text data is a long text. The first named entity recognition algorithm is the named entity recognition algorithm for the long text.

The recognition module 502 is further configured to recognize the named entity from the second text data by using the second named entity recognition algorithm in a case where the second text data is a short text. The second named entity recognition algorithm is the named entity recognition algorithm for the short text.

In some embodiments, the first matching module 503 is further configured to search for the standard named entity whose character string matches the character string of the named entity in the standard named entity database, and search for the standard named entity whose character string matches the character string of the extended named entity in the standard named entity database in response to determining that the standard named entity whose character string matches the character string of the named entity is not found. The found standard named entity whose character string matches the character string of the named entity or the extended named entity is used as the first standard named entity.

The extended named entity may be obtained by performing the complete synonym substitution on the named entity. The extended named entity may also be obtained by performing the partial synonym substitution on the named entity.

In some embodiments, the first matching module 503 is further configured to perform the word segmentation processing on the named entity to obtain the plurality of named entity word segmentations, traverse a partial synonym mapping table according to the plurality of named entity word segmentations, and substitute at least one traversed named entity word segmentation for the synonym to obtain the extended named entity.

In some embodiments, the second matching module 504 is further configured to determine the word vector similarity between each standard named entity in the standard named entity database and the named entity based on the word vector similarity matching algorithm, and determine the standard named entity whose word vector similarity to the named entity in the standard named entity database satisfies the preset condition as the second standard named entity.

In some embodiments, the second matching module 504 is further configured to calculate the length of the LOS of the named entity and each standard named entity in the standard named entity database, sequence standard named entities in the standard named entity database to obtain a standard named entity candidate list according to lengths of the longest common subsequences; and sequentially input each standard named entity in the standard named entity candidate list and the named entity into a semantic model based on a word vector, so as to obtain the word vector similarity between the named entity and the standard named entity.

The semantic model based on the word vector may include the BERT model. The fully connected layer of the BERT model may be implemented by using the softmax classifier or the sigmoid classifier.

The beneficial effects of the normalized processing apparatus 500 of the named entity provided by some embodiments of the present disclosure are the same as the beneficial effects of the normalized processing method of the named entity as described in some embodiments described above, which will not be repeated here.

Figure 6A:
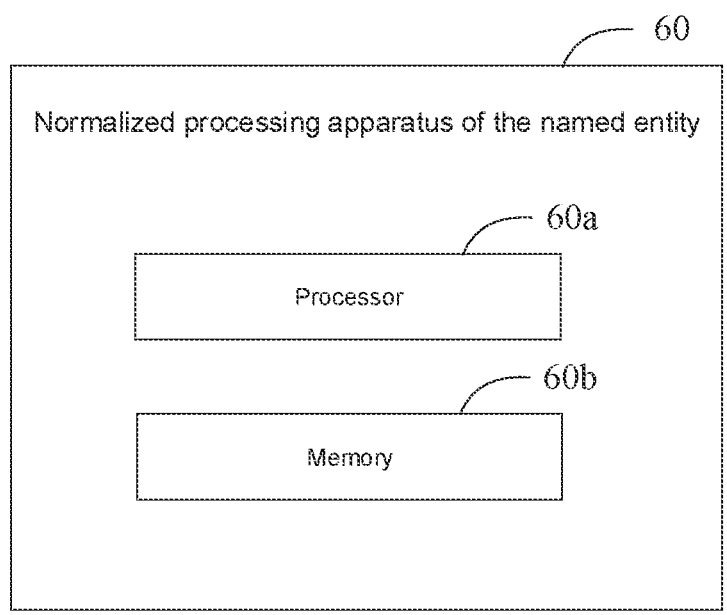
FIG. 6A is a schematic diagram of another normalized processing apparatus of a named entity, in accordance with some embodiments.

In addition, some embodiments of the present disclosure also provide another normalized processing apparatus of the named entity. As shown in FIG. 6A, the normalized processing apparatus 60 of the named entity includes one or more processors 60a and a memory 60b. The memory stores computer program instructions thereon that may run on the one or more processors, and when the computer program instructions run on the one or more processors, the normalized processing method of the named entity provided by any one of the above embodiments of the present disclosure may be performed.

For example, the one or more processors 60a are configured to obtain first text data, recognize a named entity from the first text data, determine whether a first standard named entity exists in a standard named entity database according to the named entity, determine the first standard named entity as a normalized representation of the named entity in response to determining that the first standard named entity exists in the standard named entity database, and obtain a second standard named entity from the standard named entity database and determine an obtained second standard named entity as the normalized representation of the named entity in response to determining that the first standard named entity does not exist in the standard named entity database. The first standard named entity is a standard named entity whose character string matches a character string of the named entity or an extended named entity. The extended named entity is obtained by performing a synonym substitution on at least part of words of the named entity. The second standard named entity is a standard named entity whose word vector similarity to the named entity in the standard named entity database satisfies a preset condition.

In some embodiments, the one or more processors 60a are further configured to delete a first text in the first text data to obtain second text data, and recognize the named entity from the second text data. The first text includes at least one stop word and/or at least one designated symbol.

In some embodiments, the one or more processors 60a are further configured to determine whether the text length of the second text data is greater than the preset text length threshold, use the second text data as the long text in response to determining that the text length of the second text data is greater than the preset text length threshold, and use the second text data as the short text in response to determining that the text length of the second text data is less than or equal to the preset text length threshold.

In some embodiments, the one or more processors 60a are further configured to use a first named entity recognition algorithm to recognize the named entity from the second text data in a case where the second text data is the long text; and use a second named entity recognition algorithm to recognize the named entity from the second text data in a case where the second text data is the short text. The first named entity recognition algorithm is a named entity recognition algorithm for the long text. The second named entity recognition algorithm is a named entity recognition algorithm for the short text.

In some embodiments, the first named entity recognition algorithm includes a named entity recognition algorithm based on a BiLSTM and a CRF.

In some embodiments, the second named entity recognition algorithm includes a named entity recognition algorithm based on a regular expression.

In some embodiments, the one or more processors 60a are further configured to search for the standard named entity whose character string matches the character string of the named entity in the standard named entity database, and search for the standard named entity whose character string matches the character string of the extended named entity in the standard named entity database in response to determining that the standard named entity whose character string matches the character string of the named entity is not found. The found standard named entity whose character string matches the character string of the named entity or the extended named entity is used as the first standard named entity.

In some embodiments, the extended named entity is obtained by performing a complete synonym substitution on the named entity. The complete synonym substitution is a synonym substitution on the named entity as a whole.

In some embodiments, the extended named entity is obtained by performing a partial synonym substitution on the named entity. the partial synonym substitution is a synonym substitution on at least one named entity word segmentation obtained by performing a word segmentation processing on the named entity.

In some embodiments, the one or more processors 60a are further configured to perform the word segmentation processing on the named entity to obtain a plurality of named entity word segmentations; traverse a partial synonym mapping table according to the plurality of named entity word segmentations, and substitute at least one traversed named entity word segmentation for a synonym to obtain the extended named entity.

In some embodiments, the one or more processors 60a are further configured to determine a word vector similarity between each standard named entity in the standard named entity database and the named entity based on a word vector similarity matching algorithm; and determine the standard named entity whose word vector similarity to the named entity in the standard named entity database satisfies the preset condition as the second standard named entity.

In some embodiments, the preset condition is that the word vector similarity between the named entity and the standard named entity reaches a preset similarity threshold, or the preset condition is that the named entity and one standard named entity have the highest word vector similarity.

In some embodiments, the one or more processors 60a are further configured to calculate a length of a longest common subsequence of the named entity and each standard named entity in the standard named entity database; sequence standard named entities in the standard named entity database to obtain a standard named entity candidate list according to lengths of the longest common subsequences; and sequentially input each standard named entity in the standard named entity candidate list and the named entity into a semantic model based on a word vector, so as to obtain the word vector similarity between the named entity and the standard named entity.

In some embodiments, the semantic model based on the word vector includes the BERT model. The fully connected layer of the BERT model is implemented by using a softmax classifier or a sigmoid classifier.

The beneficial effects of the normalized processing apparatus of the named entity are the same as the beneficial effects of the normalized processing method of the named entity as described in some embodiments described above, which will not be repeated here.

In addition, some embodiments of the present disclosure also provide an electronic device corresponding to the normalized processing method of the named entity provided in some embodiments described above. The electronic device may be any device with data processing capability to perform the normalized processing method of the named entity provided by some embodiments described above.

Figure 6B:
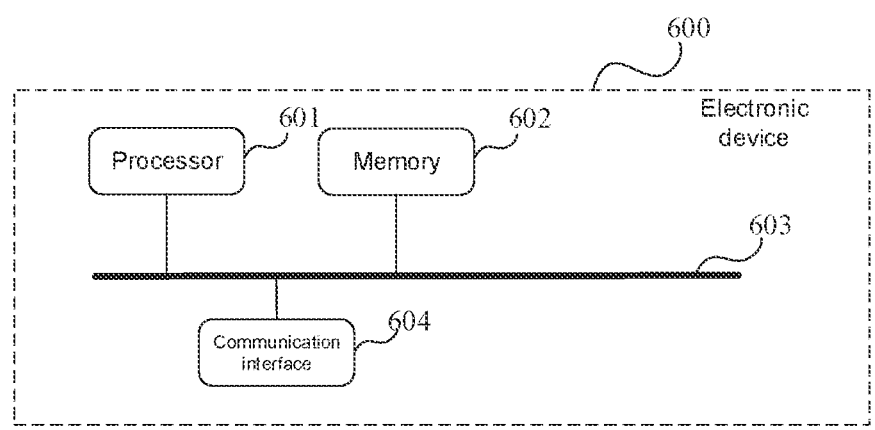
FIG. 6B is a schematic diagram of an electronic device, in accordance with some embodiments.

As shown in FIG. 6B, the electronic device 600 includes a processor 601, a memory 602, a bus 603, and a communication interface 604. The processor 601, the communication interface 604, and the memory 602 are connected through the bus 603. The memory 602 stores computer program instructions that may run on the processor 601, and when the computer program instructions runs on the processor 601, the normalized processing method of the named entity provided by any of the above embodiments of the present disclosure is executed.

The memory 602 may include a high-speed random access memory (RAM), and may also include a non-volatile memory, such as at least one disk memory. The communication connection between a network element of a system and at least one other network element is realized through at least one communication interface 604 (which may be wired or wireless), and the Internet, a wide area network, a local network, a metropolitan area network, etc. may be used.

The bus 603 may be an Industry Standard Architecture (ISA) bus, a Peripheral Component Interconnect (PCI) bus, an Extended Industry Standard Architecture (EISA) bus, etc. The bus may be classified into an address bus, a data bus, a control bus, etc. The memory 602 is used to store programs, and the processor 601 executes the programs after receiving an execution instruction. The normalized processing method of the named entity as disclosed in any one of the above embodiments of the present disclosure may be applied to the processor 601, or implemented by the processor 601.

The processor 601 may be an integrated circuit chip and has a signal processing capability. In an implementation process, steps of the above method may be implemented by using an integrated logic circuit in hardware or instructions in a software form of the processor 601. The processor 601 may be a general-purpose processor, including a central processing unit (CPU), a network processor (NP), etc.; it may also be a digital signal processor (DSP), an application specific integrated circuit (ASIC), a field-programmable gate array (FPGA), or other programmable logic devices, discrete gate or transistor logic devices, or discrete hardware components. The processor 601 may implement or execute method, steps or logical block diagrams disclosed in the embodiments of the present disclosure. The general-purpose processor may be a microprocessor or any conventional processor or the like. Steps of the method disclosed with reference to the embodiments of the present disclosure may be directly executed and completed by a hardware decoding processor, or may be executed and completed by a combination of hardware and software modules in the decoding processor. The software modules may be set in a mature storage medium in the field, such as a random access memory, a flash memory, a read-only memory, a programmable read-only memory, an electrically-erasable programmable memory, or a register. The storage medium is arranged in the memory 602, and the processor 601 reads information in the memory 602 and completes the steps in the above method in combination with hardware of the processor.

The beneficial effects of the electronic device 600 provided by some embodiments of the present disclosure are the same as the beneficial effects of the normalized processing method of the named entity as described in some embodiments described above, which will not be repeated herein.

Some embodiments of the present disclosure provide a computer-readable storage medium (e.g., a non-transitory computer-readable storage medium). The computer-readable storage medium has stored therein computer program instructions that, when executed by a computer (e.g., the normalized processing apparatus of the named entity), cause the computer to perform the normalized processing method of the named entity as described in any one of the above embodiments.

For example, the computer-readable storage medium may include, but is not limited to a magnetic storage device (e.g., a hard disk, a floppy disk or a magnetic tape), an optical disk (e.g., a compact disk (CD), a digital versatile disk (DVD)), a smart card and a flash memory device (e.g., an erasable programmable read-only memory (EPROM), a card, a stick or a key driver). Various computer-readable storage medium described in the present disclosure may represent one or more devices and/or other machine-readable storage media for storing information. The term "machine-readable storage medium" may include, but is not limited to, wireless channels and other various medium capable of storing, containing and/or carrying instructions and/or data.

In some embodiments of the present disclosure, a computer program product is also provided. The computer program product includes computer program instructions that are stored in a non-transitory computer-readable storage medium, and when the computer program instructions are executed by a computer (e.g., the normalized processing apparatus of the named entity), the computer program instructions cause the computer to perform the normalized processing method of the named entity as described in the above embodiments.

In some embodiments of the present disclosure, a computer program is also provided. When the computer program is executed by a computer (e.g., the normalized processing apparatus of the named entity), the computer program causes the computer to perform the normalized processing method of the named entity as described in the above embodiments.

The beneficial effects of the above computer-readable storage medium, computer program product, and computer program are the same as the beneficial effects of the normalized processing method of the named entity as described in some embodiments described above, which will not be repeated here.

It will be noted that the flow diagrams and block diagrams in the drawings illustrate the system architecture, functionality, and operation that may be possible to be implemented according to systems, methods and computer program products in various embodiments of the present disclosure. In this regard, each block in the flow diagrams or the block diagrams may represent a module, a program segment, or a portion of codes, which contains one or more executable instructions for implementing the specified logic function. It will also be noted that, in some alternative implementations, the functions marked in the block may also occur in an order different from the order marked in the drawings. For example, two blocks shown in succession may, in fact, be executed substantially concurrently, or the blocks may sometimes be executed in the reverse order, depending upon the functionality involved. It will also be noted that each block in the block diagrams and/or the flow diagrams, and combinations of blocks in the block diagrams and/or the flow diagrams, may be implemented by dedicated hardware-based systems that perform the specified functions or acts, or by combinations of dedicated hardware and computer instructions.

Those skilled in the art may clearly understand that, for convenience and conciseness description, the specific working processes of the systems, devices, and modules described above may refer to the corresponding processes in the foregoing method embodiments, which will not be repeated here again.

In the embodiments provided in the present disclosure, it will be understood that the disclosed apparatus and method may be implemented in other manners. The apparatus embodiments described above are merely exemplary. For example, division of the modules is merely logical function division and there may be other division manners in practical implementation. For another example, multiple modules or components may be combined or integrated into another system, or some features may be ignored or not executed. In addition, the displayed or discussed mutual coupling or direct coupling or communication connection may be indirect coupling or communication connection through some communication interfaces, and the indirect coupling or the communication connection of apparatuses or modules may be electrical, mechanical, or in other forms.

The modules described as separate parts may or may not be physically separate, and parts described as modules may or may not be physical units, the parts may be located in one position, or may be distributed in a variety of network modules. Part of or all of the modules here may be selected according to a practical need to achieve the objectives of the solutions of the embodiments.

In addition, functional modules in the embodiments of the present disclosure may be integrated into a processing unit, or each functional module may exist individually physically, or two or more than two functional modules may be integrated into one processing unit.

If the function is implemented in the form of a software functional module and sold or used as a separate product, the function may be stored in a computer-readable storage medium. Based on such understanding, the nature of the technical solutions of the present disclosure, or the part contributing to the related art in the present disclosure, or part of the technical solutions in the present disclosure may be implemented in a form of software product. The computer software product is stored in a storage medium and includes several instructions for instructing a computer device (which may be a personal computer, a server, a network device, and the like) to execute all of or part of the steps of the method described in the embodiments of the present disclosure.

Finally, it will be noted that the above embodiments are only used to illustrate the technical solutions of the present disclosure, but not limit thereto. Although the present disclosure has been described in detail with reference to the above embodiments, those skilled in the art should understand that the technical solutions described in the foregoing embodiments may be modified, or some or all of the technical features may be equivalently substituted. These modifications or replacements do not cause the essence of the corresponding technical solutions to deviate from the scope of the technical solutions of the embodiments of the present disclosure, and should all be included in the scope of the claims and the specification of the present disclosure.

What is claimed is:

1. A normalized processing method of a named entity, comprising:
    obtaining first text data;
    recognizing a named entity from the first text data;
    determining whether a first standard named entity exists in a standard named entity database according to the named entity, the first standard named entity being a standard named entity whose character string matches a character string of one of the named entity and an extended named entity, and the extended named entity being obtained by performing a synonym substitution on at least part of words of the named entity;
    determining the first standard named entity as a normalized representation of the named entity in response to determining that the first standard named entity exists in the standard named entity database; and
    obtaining a second standard named entity from the standard named entity database, and determining an obtained second standard named entity as the normalized representation of the named entity in response to determining that the first standard named entity does not exist in the standard named entity database, the second standard named entity being a standard named entity whose word vector similarity to the named entity in the standard named entity database satisfies a preset condition, wherein obtaining the second standard named entity from the standard named entity database, includes:
  determining a word vector similarity between each standard named entity in the standard named entity database and the named entity based on a word vector similarity matching algorithm; and
  determining the standard named entity whose word vector similarity to the named entity in the standard named entity database satisfies the preset condition as the second standard named entity, wherein determining the word vector similarity between each standard named entity in the standard named entity database and the named entity based on the word vector similarity matching algorithm, includes:
    calculating a length of a longest common subsequence of the named entity and each standard named entity in the standard named entity database;
    sequencing standard named entities in the standard named entity database to obtain a standard named entity candidate list according to lengths of the longest common subsequences; and
    sequentially inputting each standard named entity in the standard named entity candidate list and the named entity into a semantic model based on a word vector, so as to obtain the word vector similarity between the named entity and the standard named entity, wherein the semantic model based on the word vector includes a bi-directional encoder representation from transformers (BERT) model; and a fully connected layer of the BERT model is implemented by using a softmax classifier or a sigmoid classifier.

2. The normalized processing method according to claim 1, wherein recognizing the named entity from the first text data, includes:
  deleting a first text in the first text data to obtain second text data, the first text including at least one stop word and/or at least one designated symbol; and
  recognizing the named entity from the second text data.

3. The normalized processing method according to claim 2, wherein the second text data is a long text, and recognizing the named entity from the second text data, includes:
  using a first named entity recognition algorithm to recognize the named entity from the second text data, the first named entity recognition algorithm being a named entity recognition algorithm for the long text.

4. The normalized processing method according to claim 3, wherein before recognizing the named entity from the second text data, recognizing the named entity from the first text data, further includes:
  determining whether a text length of the second text data is greater than a preset text length threshold;
  using the second text data as the long text in response to determining that the text length of the second text data is greater than the preset text length threshold.

5. The normalized processing method according to claim 3, wherein the first named entity recognition algorithm includes a named entity recognition algorithm based on a bi-directional long-short term memory network (BiLSTM) and a conditional random field (CRF).

6. The normalized processing method according to claim 2, wherein the second text data is a short text, and recognizing the named entity from the second text data, includes:
  using a second named entity recognition algorithm to recognize the named entity from the second text data, the second named entity recognition algorithm being a named entity recognition algorithm for the short text.

7. The normalized processing method according to claim 6, wherein before recognizing the named entity from the second text data, recognizing the named entity from the first text data, further includes:
  determining whether a text length of the second text data is greater than a preset text length threshold;
  using the second text data as the short text in response to determining that the text length of the second text data is less than or equal to the preset text length threshold.

8. The normalized processing method according to claim 6, wherein the second named entity recognition algorithm includes a named entity recognition algorithm based on a regular expression.

9. The normalized processing method according to claim 1, wherein determining whether the first standard named entity exists in the standard named entity database according to the named entity, includes:
  searching for the standard named entity whose character string matches the character string of the named entity in the standard named entity database; and
  searching for the standard named entity whose character string matches the character string of the extended named entity in the standard named entity database in response to determining that the standard named entity whose character string matches the character string of the named entity is not found,
  wherein the found standard named entity whose character string matches the character string of the named entity or the extended named entity is used as the first standard named entity.

10. The normalized processing method according to claim 9, wherein the extended named entity is obtained by performing a complete synonym substitution on the named entity, and the complete synonym substitution is a synonym substitution on the named entity as a whole.

11. The normalized processing method according to claim 9, wherein the extended named entity is obtained by performing a partial synonym substitution on the named entity, and the partial synonym substitution is a synonym substitution on at least one named entity word segmentation obtained by performing a word segmentation processing on the named entity.

12. The normalized processing method according to claim 11, wherein performing the partial synonym substitution on the named entity, includes:
  performing the word segmentation processing on the named entity to obtain a plurality of named entity word segmentations; and
  traversing a partial synonym mapping table according to the plurality of named entity word segmentations, and substituting at least one traversed named entity word segmentation for a synonym to obtain the extended named entity.

13. The normalized processing method according to claim 1, wherein the preset condition is that the word vector similarity between the named entity and the standard named entity reaches a preset similarity threshold, or the preset condition is that the named entity and one standard named entity in the standard named entity database have a highest word vector similarity.

14. A normalized processing apparatus of a named entity, comprising: a memory, at least one processor, and computer program instructions stored on the memory and run on the at least one processor, wherein when the computer program instructions run on the at least one processor, the at least one processor is configured to:

obtain first text data; recognize a named entity from the first text data;

determine whether a first standard named entity exists in a standard named entity database according to the named entity; determine the first standard named entity as a normalized representation of the named entity in response to determining that the first standard named entity exists in the standard named entity database; and obtain a second standard named entity from the standard named entity database and determine an obtained second standard named entity as the normalized representation of the named entity in response to determining that the first standard named entity does not exist in the standard named entity database;

wherein the first standard named entity is a standard named entity whose character string matches a character string of one of the named entity and an extended named entity;

the extended named entity is obtained by performing a synonym substitution on at least part of words of the named entity;

the second standard named entity is a standard named entity whose word vector similarity to the named entity in the standard named entity database satisfies a preset condition;

wherein that the at least one processor is configured to obtain the second standard named entity from the standard named entity database, includes:

determining a word vector similarity between each standard named entity in the standard named entity database and the named entity based on a word vector similarity matching algorithm; and determining the standard named entity whose word vector similarity to the named entity in the standard named entity database satisfies the preset condition as the second standard named entity, wherein that the at least one processor is configured to determine the word vector similarity between each standard named entity in the standard named entity database and the named entity based on the word vector similarity matching algorithm, includes:

calculating a length of a longest common subsequence of the named entity and each standard named entity in the standard named entity database;

sequencing standard named entities in the standard named entity database to obtain a standard named entity candidate list according to lengths of the longest common subsequences; and sequentially inputting each standard named entity in the standard named entity candidate list and the named entity into a semantic model based on a word vector, so as to obtain the word vector similarity between the named entity and the standard named entity, wherein the semantic model based on the word vector includes a bi-directional encoder representation from transformers (BERT) model; and a fully connected layer of the BERT model is implemented by using a softmax classifier or a sigmoid classifier.

15. An electronic device, comprising: a memory, a processor, and computer program instructions stored on the memory and run on the processor, wherein when the processor executes the computer program instructions, the electronic device performs one or more steps of the normalized processing method according to claim 1.

16. A non-transitory computer-readable storage medium storing computer program instructions that, when executed by a computer, cause the computer to perform one or more steps of the normalized processing method according to claim 1.

17. A computer program product comprising computer program instructions that are stored in a non-transitory computer-readable storage medium, wherein when executed by a computer, the computer program instructions cause the computer to perform one or more steps of the normalized processing method according to claim 1.

* * * * *